United States Patent [19]

Simonovitch

[11] 4,426,522
[45] Jan. 17, 1984

[54] HEXAHYDRO-1,2,4-TRIAZINE-3,5 DIONE DERIVATIVES

[75] Inventor: Chaim Simonovitch, Rishon L'etzion, Israel

[73] Assignee: ABIC Ltd., Israel

[21] Appl. No.: 347,355

[22] Filed: Feb. 9, 1982

[30] Foreign Application Priority Data

Feb. 18, 1981 [IL] Israel .................................. 62151

[51] Int. Cl.$^3$ ............................................ C07D 253/06
[52] U.S. Cl. .................................................... 544/182
[58] Field of Search ........................................ 544/182

[56] References Cited

U.S. PATENT DOCUMENTS 4,297,129 10/1981 Sanemitsu et al. .................. 544/182

OTHER PUBLICATIONS

Novacek et al., *Coll. czech. Chem. Commun.* vol. 39, pp. 3760–3762 (1973).

*Primary Examiner*—John M. Ford
*Attorney, Agent, or Firm*—Steinberg & Raskin

[57] ABSTRACT

The invention provides new hexahydro-1,2,4-triazine-3,5-dione derivatives having anticoccidiastatic activity, to the production thereof and to their use as part of a feed and/or pre-feed mixture.

12 Claims, No Drawings

HEXAHYDRO-1,2,4-TRIAZINE-3,5 DIONE DERIVATIVES

The present invention relates to a hexahydro-1,2,4-triazine-3,5-diones of general formula I:

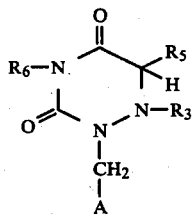

in which $R_3$ stands for a hydrogen atom or for an alkyl, tetrahydrofuryl, alkylsulfonyl radical or for a radical

in which $R_4$ stands for an alkyl radical which is optionally substituted by a halogen atom, or by an alkoxy carbonyl or by an alkoxy radical; for a phenyl radical substituted with one or more halogen atoms, nitro groups or lower alkyl groups; for a benzyl radical substituted with one or more halogen atoms; for a phenyl thio methylene or phenylaminomethylene radical substituted with one or more halogen atoms; thienyl radical optionally substituted with one or more halogen atoms or for a CO-hexahydro-1,2,4-triazine-3,5-dione; $R_5$ and $R_6$ each stand for the same or different hydrogen atom or alkyl groups and $R_6$ may stand also for an alkali or earth alkali atom; and A stands for

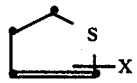

in which X stands for one or more halogen atoms; or for

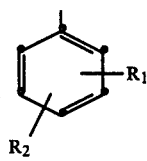

in which $R_1$ and $R_2$ each stand for the same or different hydrogen or halogen atom or for trifluoromethyl, alkyl, cyano or alkoxy radical; with the proviso that one of substituents $R_1$, $R_2$, $R_3$, $R_5$ and $R_6$ must be different from hydrogen.

In the above formulae the alkyl and alkoxy groups are preferably lower alkyl and lower alkoxy groups, straight or branched, having 1–5 C atoms. The preferred halogen atoms are the chlorine and fluorine atoms. The preferred alkali atoms are the sodium and potassium atoms.

From DOS 1951828 there are known compounds of general formula II

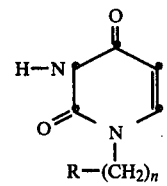

in which n may stand for 0 or 1 and R stands for a pentafluorophenyl, pentachlorophenyl, 3,4-methylenedioxyphenyl group or for a group of general formula III

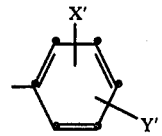

in which X' stands for a hydrogen atom, a halogen atom, a lower alkoxy, nitro-trichloromethyl or cyano group and Y' stands for a hydrogen or halogen atom or for a nitro or trifluoro methyl and when n stands for 1 Y' may stand also for an alkylsulfonyl radical with the proviso that when n stands for 1 and X' stands for hydrogen Y' stands for lower alkylsulfonyl radical.

In DOS 2423972 there are described and claimed similar compounds to that of general formula II in which formula n stands for 0 and which the phenyl nucleus is substituted by other substituents than those of R in general formula II.

It has been found that said compounds have a certain anti-coccidiostatic activity.

Many experiments have been performed by the applicants in order to test whether compounds of general formula II in which n stands for 0 and in which the double bond in the heterocyclic nucleus has been removed by way of hydrogenization have any coccidiostatic activity. No such activity could be found.

From A. Novacek and J. Gut., Coll. Czech. Chem. Commun., 39 (12) 3760-2(1973) there is known 2-benzylhexahydro-1,2,4-triazine-3,5-dione. Said compound was tested and it has been found that it does not possess any coccidiostatic activity.

It has therefore been surprisingly found that the new compounds of general formula I have very good coccidiostatic activity.

The new compounds are not mutagenic in the Ames test. They have low acute toxicity in chicks (above 2000 mg/kg).

The new compounds are administered either as a part of a pre-fed mixture or directly to the feed or in the drinking water. Suitable quantities are 50–300 preferably 70–200 ppm in the feed or in the drinking water.

The new compounds according to the present invention are prepared by hydrogenation of a compound of general formula IV

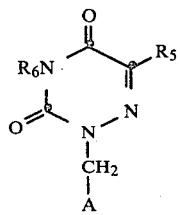

in which A, $R_5$ and $R_6$ have the same meaning as in general formula I and in case that a compound of general formula I in which $R_3$ is different from hydrogen is to be prepared the compound of general formula I obtained is converted into the desired compound by methods known per se.

The hydrogenation is preferably performed with zinc and acetic acid advantageously in an inert solvent such as benzene, pyridine acetone, dimethoxyethane or tetrahydrofuran. In some instances an excess of acetic acid may serve as solvent.

The reaction is preferably performed at a temperature range of 50° to the boiling point of the solvent. (All temperatures herein are given in degrees Centigrade). The time required is 3-4 hours depending on the reaction conditions. The compounds of general formula IV are either known or can easily be prepared by the method as described by A. Novacek and D. Hasoun Coll. Czech. Chem. Commun. 30 3890-4 (1965).

In case that $R_3$ should stand for an alkyl group the compound of general formula I obtained after hydrogenation is reacted with a suitable dialkyl sulfate under neutral or acidic conditions in an inert solvent. e.g., benzene, toluene, etc., preferably at boiling temperature.

In case that $R_3$ should stand for an alkyl sulfonyl radical the compound of general formula I obtained after hydrogenation is preferably reacted with a suitable alkane sulfonyl halide in an inert basic solvent, e.g., pyridine, at ambient temperature.

In case that $R_3$ should stand for a $COR_4$ radical the compound of general formula I obtained after hydrogenation is preferably reacted with a suitable acyl anhydride or halide, advantageously the chloride. Said reaction is preferably performed at reflux temperature in an inert solvent, e.g., benzene, toluene, tetrahydrofuran, dimethoxyethane, dioxane, etc. Sometimes the anhydride or halide is used in excess and then serves also as solvent.

In case that $R_4$ stands for $CH_2Cl$ the compound obtained may be reacted with $HSC_6H_5$ or $H_2NC_6H_5$ in order to obtain the phenylthiomethylene or phenylaminoethylene derivative.

In case that $R_6$ should stand for an alkyl group it may be prepared by direct hydrogenation of the corresponding compound. However, sometimes it is advantageous to prepare the compound of general formula I in which $R_6$ stands for hydrogen and to alkylate it, e.g., with a dialkyl sulfate under basic conditions, e.g. with the addition of $Na_2CO_3$.

In case that $R_6$ should stand for an alkali or earth alkali atom the compound of general formula I, which $R_6$ stands for a hydrogen atom is reacted with an aqueous solution of the appropriate base.

The present invention will now be illustrated with reference to the following examples without being limited by them. All melting points in said examples are uncorrected. All compounds have been identified by way of elemental analysis, infra red and n.m.r. spectra.

EXAMPLE 1

In a three-necked flask equipped with a mechanical stirrer and a reflux condenser, 2 g of 1-(2'-chlorobenzyl)-6-aza uracil was suspended in 200 ml of water and 40 ml of glacial acetic acid was added. 2.2 g of powdered zinc was added in small portions to the admixture. After all the zinc had been added the mixture was vigorously stirred and refluxed for 24 hours. The solution obtained was cooled and filtered. The precipitate was dissolved in boiling methanol and the solution filtered. After standing overnight 2-(2'-chlorobenzyl)hexahydro-1,2,4-triazine-3,5 dione precipitated as white crystals; m.p. 200°; yield 1 g (50%).

In the same manner were prepared:
a. 2-(3'-chlorobenzyl)-hexahydro-1,2,4-triazine-3,5-dione; m.p. 168°; yield 50%.
b. 2-(4'-chlorobenzyl)-hexahydro-1,2,4-triazine-3,5-dione; m.p. 210°; yield 50%.
c. 2-(5'-chloro-2'-thienyl-methylene)-hexahydro-1,2,4-triazine 3,5-dione; m.p. 148°; yield 40%.

EXAMPLE 2

Into a three-necked flask equipped with a mechanical stirrer and a condenser were placed 300 ml of water, and stirring was commenced. 3 g of 1-(2',4'-dichlorobenzyl)-6-aza uracil were added and after a fine suspension had been obtained, of 60 ml of glacial acetic acid was added to this suspension. 3.3 g of fine zinc powder was then added in small portions. After all materials had been added the mixture was vigorously stirred and refluxed for 24 hours. The completion of the reduction was verified by thin layer chromatography. The mixture was cooled and the precipitate thus formed was filtered off and redissolved in hot methanol. The undissolved material was filtered off and the methanol solution was cooled to yield 2-(2',4'-dichlorobenzyl)-hexahydro-1,2,4-triazine-3,5 dione; m.p. 230°; yield 1.4 g (60%).

In the same manner was prepared: 2-(3',4'-dichlorobenzyl)-hexahydro-1,2,4-triazine-3,5 dione; m.p. 167°; yield 50%.

The compound is not mutagenic as was found out in the Ames test.

EXAMPLE 3

Into a three-necked flask equipped with a mechanical stirrer and a reflux condenser was placed 1 g of 1-(3-methylbenzyl)-6-aza-uracil, 100 ml of water was added and a vigorous stirring commenced. 1.1 g of zinc powder was added in one portion, and was followed by dropping in 20 ml of glacial acetic acid. The mixture was then vigorously stirred and refluxed for 24 hours. The mixture was thereafter cooled and the precipitate was filtered off with suction. The mass of crystals was dissolved in hot methanol, the solution filtered and the filtrate was left to stand overnight and filtered to yield 0.6 g of 2-(3'-methylbenzyl)-hexahydro-1,2,4-triazine-3,5-dione; m.p. 158°.

In the same manner were prepared:
a. 2-(4'-methylbenzyl)-hexahydro-1,2,4-triazine-3,5-dione; m.p. 168°; yield 40%.
b. 2-(2'-methylbenzyl)-hexahydro-1,2,4-triazine-3,5-dione; m.p. 186°.
c. 2-(4'-methoxybenzyl)-hexahydro-1,2,4-triazine-3,5-dione; m.p. 98°.

EXAMPLE 4

A 1 liter three-necked flask equipped with a mechanical stirrer was charged with 300 ml of water and 60 ml of glacial acetic acid. 3 g of 1-(3'-trifluoromethylbenzyl)-6-aza uracil was added in one portion followed by the addition of 3.3 g of zinc powder in small portions. After the addition was terminated the mixture was stirred vigorously and refluxed for 36 hours after which the mixture was cooled in ice and filtered. The crystals obtained were recrystallized from iso-propanol to give 1.5 g (50%) of 2-(3'-trifluoromethylbenzyl)-hexahydro-1,2,4-triazine-3,5-dione; m.p. 152°.

In the same manner were prepared:
a. 2-(3'-fluorobenzyl)-hexahydro-1,2,4-triazine-3,5-dione; m.p. 175°; yield 50%.
b. 2-(4'-cyanobenzyl)-hexahydro-1,2,4-triazine-3,5-dione; m.p. 250°; yield 30%.
c. 2-(2'-cyanobenzyl)-hexahydro-1,2,4-triazine-3,5-dione; m.p. 215°; yield 30%.

EXAMPLE 5

Into a 100 ml round bottomed flask equipped with an efficient condenser and a calcium chloride tube were placed 10 ml of acetic anhydride and 0.5 g of 2-(4'-chlorobenzyl)-hexahydro-1,2,4-triazine-3,5 dione. The mixture was refluxed for 3 hours, then was cooled and poured on ice water, and left overnight. The crystals that separated were filtered off by suction and dried. The product was recrystallized from isopropanol to give 0.3 g (60%) of 1-acetyl-2-(4'-chlorobenzyl)-hexahydro-1,2,4-triazine-3,5-dione; m.p. 100°.

In the same manner was prepared: 1-acetyl-2-(3',4'-dichlorobenzyl)-hexahydro-1,2,4-triazine-3,5-dione; m.p. 97°; yield 85%.

EXAMPLE 6

Into a 100 ml round bottom flask equipped with an efficient condenser and a calcium chloride tube were placed 5 g of dichloroacetylchloride and 0.5 g of 2-(3'-4'-dichloro-benzyl)hexahydro-1,2,4-triazine-3,5-dione, and the mixture obtained was refluxed for 3 hours. The solvent was then removed under vacuum. 10 ml of cold water was added then the solution was neutralized with a saturated aqueous solution of sodium bicarbonate. The crystals that precipitated were filtered off by suction and recrystallized from isopropanol to give 0.5 g of 1-dichloroacetyl-2-(3',4'-dichlorobenzyl)-hexahydro-1,2,4-triazine-3,5-dione; m.p. 196°.

In the same manner were prepared:
a. 1-dichloroacetyl-2-(2',4'-dichlorobenzyl)-hexahydro-1,2,4-triazine-3,5-dione; m.p. 210°; yield 37%.
b. 1-dichloroacetyl-2-(4'-chlorobenzyl)-hexahydro-1,2,4-triazine-3,5 dione; m.p. 195°; yield 75%.
c. 1-dichloroacetyl-2-(2'-chlorobenzyl)-hexahydro-1,2,4-triazine-3,5 dione; m.p. 135°; yield 40%.
d. 1-dichloroacetyl-2-(3'-chlorobenzyl)-hexahydro-1,2,4-triazine-3,5-dione; m.p. 202°; yield 40%.
e. 1-dichloroacetyl-2-(3'-trifluoromethyl)-hexahydro-1,2,4-triazine-3,5-dione; m.p. 165°; yield 40%.
f. 1-dichloroacetyl-2-(4'-cyanobenzyl)-hexahydro-1,2,4-triazine-3,5-dione; m.p. 202°.

EXAMPLE 7

Into a 50 ml round bottomed flask equipped with an efficient condenser sealed with a calcium chloride tube were placed 10 ml of ethylchloroformate and 1 g of 2-(4'-chlorobenzyl)-hexahydro-1,2,4-triazine-3,5-dione. The mixture was refluxed for 3 hours, the solvent was removed in vacuum and ice water was added cautiously to the residue. The solution was adjusted to a neutral pH with a saturated solution of sodium bicarbonate. The crystals thus formed were filtered off by suction and recrystallized from isopropanol to yield 0.8 g (50%) of 1-ethoxycarbonyl-2-(4'-chlorobenzyl)-hexahydro-1,2,4-triazine-3,5-dione; m.p. 135°.

In the same manner was prepared: 1-ethoxycarbonyl-2-(3',4'-dichlorobenzyl)-hexahydro-1,2,4-triazine-3,5-dione; m.p. 120°; yield 40%.

EXAMPLE 8

Into a 50 ml round bottomed flask equipped with a calcium chloride drying tube and a magnetic stirrer were placed 5 ml of dry pyridine and 1 g of 2-(4'-chlorobenzyl)-hexahydro-1,2,4-triazine-3,5 dione. The mixture was then stirred and cooled in an ice bath, 0.5 g of methanesulfonyl chloride was added dropwise. After the product had been added the mixture was brought to ambient temperature and stirred for 5 hours. The solvent was then removed in vacuum and the residue was neutralized with dilute hydrochloric acid. The crystals obtained were filtered off and recrystallized from alcohol to yield 0.8 g of 1-methane sulfonyl-2-(4'-chlorobenzyl)-hexahydro-1,2,4-triazine-3,5-dione; m.p. 145°.

In the same manner was prepared: 1-methanesulfonyl-2-(3',4'-dichlorobenzyl)-hexahydro-1,2,4-triazine-3,5 dione; m.p. 180°.

EXAMPLE 9

Into a 100 ml round bottomed flask equipped with a reflux condenser sealed with a calcium chloride tube, were placed 100 ml of dry benzene, 1 g of 2-(4'-chlorobenzyl)-hexahydro-1,2,4-triazine-3,5-dione and 2 ml of p-chlorobenzoylchloride. The mixture was refluxed for 18 hours, the solution obtained was then cooled and the precipitated crystals were filtered off by suction to yield 1 g (60%) of 1-(4'-chlorobenzoyl)-2-(4'-chlorobenzyl)-hexahydro-1,2,4-triazine-3,5-dione; m.p. 205°.

In the same manner was prepared: 1-(2'-methyl-3',5'-dinitrobenzoyl)-2-(4'-chlorobenzyl)-hexahydro-1,2,4-triazine-3,5-dione; m.p. 202°.

EXAMPLE 10

Into a 100 ml round bottomed flask fitted with a reflux condenser sealed with a calcium chloride tube and a magnetic stirrer were placed 15 ml of chloroacetylchloride and 1 g of 2-(4'-chlorobenzyl)-hexahydro-1,2,4-triazine-3,5 dione. The mixture obtained was refluxed for 18 hours. The mixture was then cooled and poured onto water and neutralized with a saturated solution of NaHCO₃. The precipitated crystals were filtered off and recrystallized from isopropanol to yield 0.8 g (53%) of 1-chloroacetyl-2-(4'-chlorobenzyl)-hexahydro-1,2,4-triazine-3,5 dione; m.p. 147°.

EXAMPLE 11

1 g of 1-chloroacetyl-2-(4'-chlorobenzyl)-hexahydro-1,2,4-triazine-3,5 dione and 0.45 g of parachlorothiophenol were added to 30 ml of dry dimethyl formamide in a 100 ml round bottomed flask fitted with a reflux condenser and a magnetic stirrer. The mixture was stirred and heated at 50° for 24 hours. The mixture was then poured onto 100 ml of ice water. The precipitated crystals were filtered off and dried to yield 0.5 g (30%)

of 1-(4'-chlorophenyl-thioacetyl)-2-(4'-chlorobenzyl)-hexahydro-1,2,4-triazine-3,5-dione-hydrate; m.p. 100°.

EXAMPLE 12

Into a 100 ml round bottomed flask fitted with a reflux condenser sealed with a calcium chloride tube and a magnetic stirrer, were placed 55 g of 2-chlorophenylacetyl chloride and 20 ml of dry benzene. Stirring was commenced and 1 g of 2-(4'-chlorobenzyl)-hexahydro-1,2,4-triazine-3,5-dione was added in one portion and the mixture was stirred and refluxed for 8 hours. The mixture was then cooled and the precipitated crystals were filtered off and recrystallized from isopropanol to yield 0.3 g of 1-(2'-chlorophenylacetyl)-2-(4'-chlorobenzyl)-hexahydro-1,2,4-triazine-3,5-dione; m.p. 224°.

In the same manner were prepared:
a. 1-(2'-chlorophenylacetyl)-2-(3',4'-dichlorobenzyl)-hexahydro-1,2,4-triazine-3,5-dione; m.p. 172°; yield 45%.
b. 1-(4'-chlorophenylacetyl)-2-(3',4'-dichlorobenzyl)-hexahydro-1,2,4-triazine-3,5-dione; m.p. 164°.

EXAMPLE 13

20 ml of dry benzene was placed into a 50 ml round bottomed flask equipped with a reflux condenser sealed with a calcium chloride tube. 0.6 g of 2-thiophene carbonyl chloride and 1 g of 2-(2',4'-dichlorobenzyl)-hexahydro-1,2,4-triazine-3,5 dione were added and the mixture was stirred for 3 hours with reflux. The solution obtained was then cooled in an ice bath and the precipitated crystals were filtered off by suction and then recrystallized from isopropanol to yield 1 g of 1-(2'-thenoyl-2-(3',4'-dichlorobenzyl)-hexahydro-1,2,4-triazine-3,5-dione; m.p. 174°.

In the same manner was prepared: 1-(2'-thenoyl)-2-(4'-chlorobenzyl)-hexahydro-1,2,4-triazine-3,5-dione; m.p. 188°.

EXAMPLE 14

Into a 100 ml round bottomed flask equipped with a reflux condenser and sealed with a calcium chloride tube, were placed 30 ml of dry benzene. 1.35 g of 2-(3',4'-dichlorobenzyl)-hexahydro-1,2,4-triazine-3,5-dione and 0.63 g of oxalyl chloride were added and this mixture was stirred and refluxed for 4 hours. The solvent was removed in vacuum and the residue was triturated with a little water. The crystals that were formed were filtered off by suction to give 1.42 g (94%) of 1,1'-oxalyl-2-(3',4'-dichlorobenzyl)-hexahydro-1,2,4-triazine-yl-3,5-dione; m.p. 245°.

In the same manner were prepared:
a. 1-ethoxycarbonyl-2-(4'-chlorobenzyl)-6-methyl-hexahydro-1,2,4-triazine-3,5-dione;
b. 1-ethoxycarbonyl-2-(3',4'-dichlorobenzyl)-6-methyl-hexahydro-1,2,4-triazine-3,5-dione; m.p. 190°.

EXAMPLE 15

200 ml of water was charged to a 500 ml round bottomed three necked flask fitted with an efficient mechanical stirrer and a reflux condenser. 40 ml of glacial acetic acid and 2 g of 1-(4'-chlorobenzyl)-6-azathyamidine were added; stirring was commenced and 2.2 g of zinc powder was added in portions. The mixture was then stirred and refluxed overnight. The solution obtained was cooled in an ice bath, the precipitated crystals were filtered off and recrystallized from isopropanol to yield 1 g (50%) of -2-(4'-chlorobenzyl)-6-methyl-hexahydro-1,2,4-triazine-3,5-dione; m.p. 165°.

In the same manner was prepared: 2-(3',4'-dichlorobenzyl)-6-methyl-hexahydro-1,2,4-triazine-3,5-dione; m.p. 155°; yield 60%.

EXAMPLE 16

Into a 50 ml round bottomed flask equipped with an efficient stirrer and a reflux condenser (sealed with a calcium chloride tube) were introduced 20 ml of dry benzene, 0.6 g of potassium carbonate, 1 g of 2-(4'-chlorobenzyl)-hexahydro-1,2,4-triazine-3,5 dione and 0.5 g of dimethyl sulphate. The mixture was stirred and refluxed for 24 hours. The mixture was cooled and filtered. The solvent was removed and the residue was column chromatographed on 75 g silica gel. 4-methyl-2-(4'-chlorobenzyl)-hexahydro-1,2,4-triazine-3,5-dione was eluted with chloroform; m.p. 128°-130°. The structure was identified by n.m.r. spectrum: 4.60 (S, $\phi$-CH$_2$N<), 3.625 (S, CH$_2$ ring) 3.16 (S,

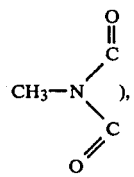

complex aromatic 7.37 (3H)

EXAMPLE 17

Into a 50 ml round bottomed flask equipped with an efficient stirrer and a reflux condenser (sealed with a calcium chloride tube), were introduced 0.5 g of dimethyl sulfate, 20 ml of dry benzene and 1 g of 2-(3'4'-dichlorobenzyl)-hexahydro-1,2,4-triazine-3,5 dione. The mixture was stirred and refluxed overnight. The solvent was then evaporated and the residue was column chromatographed on 150 g of silica gel. 1-methyl-2-(3',4'-dichlorobenzyl)-hexahydro-1,2,4-triazine-3,5-dione was eluted out with 2% methanol in chloroform; m.p. 82°-83°.

The structure was established by n.m.r. spectrum: 1H, 8.565 (NH), 2H, 4.545 (S, $\phi$CH$_2$—N<) 2H, 3.625 (S, CH$_2$ ring), 3H, 2.595 (CH$_3$—N).

EXAMPLE 18

0.5 g of 2-(4'-chlorobenzyl)-hexahydro-1,2,4-triazine-3,5-dione was added to 2.23 ml of 1 N NaOH. 50 ml of water was then added and the mixture obtained was stirred for 3 hours until a practically clear solution resulted. The solution was filtered and the water was removed by lyophillization to yield 0.54 g of 2-(4'-chlorobenzyl)-4-sodium-hexahydro-1,2,4-triazine-3,5-dione; m.p. 192° (decomp.).

EXAMPLE 19

0.5 g of 2-(3',4'-dichlorobenzyl)-hexahydro-1,2,4-triazine-3,5-dione was added to 1.83 ml of 1 N NaOH, 50 ml of water was then added and the suspension was stirred for 8 hours until a practically clear solution was obtained. The solution was filtered and the water removed by lyophillization. The 2-(3',4'-dichlorobenzyl)-4-sodium-hexahydro-1,2,4-triazine was obtained as crystalline entity m.p. 120° (decomp.); yield 0.5 g.

EXAMPLE 20

1 g of 2-(4'-chlorobenzyl)-hexahydro-1,2,4-triazine-3,5-dione, 0.8 g of 2-acetoxytetrahydrofuran. 50 ml of acetonitrile and 50 mg of sodium iodide were mixed and placed in a sealed steel bomb that was heated for 6 hours at 100°. The solvent was removed and the residue was chromatographed on silica gel. Elution with 5% methanol in chloroform gave 200 mg of oily 1-(2'-tetrahydrofuryl)-2-(4'-chlorobenzyl)-hexahydro-1,2,4-triazine-3,5-dione that was recrystallized from petroleum ether 40°-60°; m.p. 128°-30°.

EXAMPLE 21

Compounds of formula I were tested for anticoccidial activity in 10 days chicks according to the following procedure: groups of 6-8, ten day old chicks were each infected orally with $2 \times 15^5$ sporulated oocysts of Eimeria tenella. Drugs were administered as a mixture in laying hens feed without any additives (vitamin K, antibiotics) at the day of the infection and continuing for 6 days. The surviving chicks were then sacrificed and the following parameters were defined: weight, caecal lesions and oocyst count. Caecal lesions of the surviving chicks were screened on a scale of 0,1,2,3 and any dead chicks with lesions scored at 4. The activity of the drugs is expressed as follows for each group (+++) mean lesion score of 0.0 to 0.9 (++) mean lesion score of 1.0 to 1.9 (+) mean lesion score of 2.0 to 3.5. The results indicated in Table I were recorded:

TABLE I

| Example | A | $R_3$ | $R_5$ | $R_6$ | Activity (conc. in p.p.m.) |
|---|---|---|---|---|---|
| 1 | 4-Cl-phenyl | H | H | H | +++(200) ++(100) ++(70) |
| 6b | 4-Cl-phenyl | COCHCl$_2$ | H | H | +++(200) +++(100) ++(70) |
| 10 | 4-Cl-phenyl | COCH$_2$Cl | H | H | ++(200) ++(100) |
| 7 | 4-Cl-phenyl | CO$_2$C$_2$H$_5$ | H | H | +++(150) |
| 12 | 4-Cl-phenyl-COCH$_2$- | 2-Cl-phenyl | H | H | ++(125) |
| 2; 24 | 3,4-diCl-phenyl | H | H | H | +++(70) |
| 8 | 3-Cl-phenyl | SO$_2$CH$_3$ | H | H | ++(200) |
| 7a | 2,6-diCl-phenyl | CO$_2$C$_2$H$_5$ | H | H | +++(100) |
| 13 | 3,4-diCl-phenyl | 5-CO-thien-2-yl | H | H | +++(200) |
| 15 | 3-Cl-phenyl | H | CH$_3$ | H | ++(200) |

EXAMPLE 22

140 g of 2-(4'-chlorobenzyl)-hexahydro-1,2,4-triazine-3,5 dione and 860 g of calcium carbonate were mixed with an efficient mixer to produce a 12.5% premix. The premix is mixed with 2 tons of poultry feed to give a final concentration of 70 ppm.

EXAMPLE 23

Finely divided 200 g of 2-(3',4'-dichlorobenzyl)-hexahydro-1,2,4-triazine; 3,5 dione and 800 g of almond peels were mixed together to give a 20% premix of the active ingredient. The premix is mixed with 2 tons of poultry feed to give a final concentration of 100 ppm.

EXAMPLE 24

2 g of 2(3',4'-dichlorobenzyl)-6-aza uracil were suspended in 40 ml of glacial acetic acid. The mixture was stirred and heated to 100° C., 2.2 g of zinc powder was added at that temperature in small portions during 10 minutes. The mixture was heated at 100° C. for 1 hour and the solvent was removed in vacuo. The residue was dissolved in 20 ml of hot water, the solution was filtered and cooled to give 1.2 g of 2'-(3'4'-dichlorobenzyl)-1,2,4-hexahydro triazine-3,5 dione.

In a resistance built up study with chicks infected with sub-effective doses of the compound no resistance was observed of Emeria tenella in 11 passages.

I claim:

1. A compound of the formula:

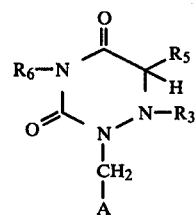

wherein R³ is hydrogen, lower alkyl, tetrahydrofuryl, lower alkylsulfonyl or

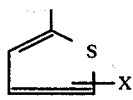

wherein R₄ is lower alkyl, lower alkyl substituted by halogen, lower alkoxy or lower alkoxy carbonyl, or R₄ is phenyl substituted with at least one halogen, nitro or lower alkyl, or R₄ is benzyl substituted by at least one halogen, or R₄ is phenyl thio methylene or phenyl amino methylene substituted by at least one halogen, or R₄ is thienyl or thienyl substituted with at least one halogen atom or CO-hexahydro-1,2,4-triazine-3,5-dione, wherein R₅ is hydrogen or lower alkyl, wherein R₆ is hydrogen, lower alkyl, alkali metal or alkaline earth metal, and wherein A is

wherein X is at least one halogen, or A is

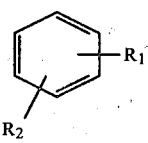

wherein R₁ and R₂ are each hydrogen, halogen, trifluoromethyl, lower alkyl, cyano or lower alkoxy, and wherein at least one of the substituents R₁, R₂, R₃, R₅ and R₆ must be other than hydrogen.

2. Compound according to claim 1 wherein the halogen is chlorine or fluorine.

3. Compound according to claim 1, wherein the alkali is sodium or potassium.

4. A compound of claim 1 being 2-(2'-chlorobenzyl)-hexahydro-1,2,4-triazine-3,5 dione.

5. A compound of claim 1 being 2-(3'-chlorobenzyl)-hexahydro-1,2,4-triazine-3,5 dione.

6. A compound of claim 1 being 2-(4'-chlorobenzyl)-hexahydro-1,2,4-triazine-3,5 dione.

7. A compound of claim 1 being 2-(2',4'-dichlorobenzyl) hexahydro-1,2,4-triazine-3,5 dione.

8. A compound of claim 1 being 2-(3',4'-dichlorobenzyl)-hexahydro-1,2,4-triazine-3,5 dione.

9. A compound of claim 1 being 1-(2'-methyl-3',5'-dinitrobenzoyl)-2-(4'-chlorobenzyl)-hexahydro-1,2,4-triazine-3,5-dione.

10. A compound of claim 1 being 1-chloroacetyl-2-(4'-chlorobenzyl)-hexahydro-1,2,4-triazine-3,5-dione.

11. A compound of claim 1 being 2-(4'-chlorobenzyl)-4-sodium-hexahydro-1,2,4-triazine-3,5-dione.

12. A compound of claim 1 being 2-(3',4'-dichlorobenzyl)-4-sodium-hexahydro-1,2,4-triazine.

* * * * *